US006333169B1

(12) United States Patent
Hudziak et al.

(10) Patent No.: US 6,333,169 B1
(45) Date of Patent: Dec. 25, 2001

(54) HER2 EXTRACELLULAR DOMAIN

(76) Inventors: Robert Michael Hudziak; H. Michael Shepard; Axel Ullrich, all of 460 Point San Bruno, San Francisco, CA (US) 94080

( * ) Notice: Subject to any disclaimer, the term of this patent is extended or adjusted under 35 U.S.C. 154(b) by 0 days.

(21) Appl. No.: 08/422,734

(22) Filed: Apr. 14, 1995

Related U.S. Application Data

(62) Division of application No. 08/355,460, filed on Dec. 13, 1994, now abandoned, which is a continuation of application No. 08/048,346, filed on Apr. 15, 1993, now abandoned, which is a continuation of application No. 07/354,319, filed on May 19, 1989, now abandoned.

(51) Int. Cl.$^7$ .............................. C12N 15/10; C07H 21/00

(52) U.S. Cl. .................... 435/69.1; 435/69.1; 435/240.2; 435/252.3; 435/320.1; 536/23.5

(58) Field of Search ............................. 435/69.1, 240.2, 435/252.3, 320.1; 536/23.5

(56) References Cited

U.S. PATENT DOCUMENTS

| | | |
|---|---|---|
| 4,761,371 | 8/1988 | Bell et al. . |
| 4,877,611 | 10/1989 | Cantrell . |
| 4,935,341 * | 6/1990 | Bargmann et al. .................... 435/6 |
| 4,963,354 | 10/1990 | Shepard et al. . |
| 4,968,603 | 11/1990 | Slamon et al. . |
| 5,030,576 * | 7/1991 | Dull et al. ........................... 435/69.7 |
| 5,081,228 * | 1/1992 | Dower et al. ....................... 435/69.1 |
| 5,126,433 | 6/1992 | Maddon et al. . |
| 5,183,884 * | 2/1993 | Krauss et al. ...................... 435/320.1 |
| 5,401,638 * | 3/1995 | Carney et al. ...................... 435/7.23 |

FOREIGN PATENT DOCUMENTS

| | | |
|---|---|---|
| 8901973 * | 3/1989 | (WO) . |
| WO 89/06692 | 7/1989 | (WO) ............................. C12P/21/00 |
| WO 89/01973 | 9/1989 | (WO) . |
| WO 89/10412 | 11/1989 | (WO) ............................. C12Q/1/68 |
| WO 91/02062 | 2/1991 | (WO) . |

OTHER PUBLICATIONS

Akiyama et al "The Product of the Human c–erbB–2 Gene . . ." *Science* 232:1644–1646, (Jun. 1986).
Drebin et al "Inhibition of Tumor Growth by a Monoclonal Antibody . . ." *PNAS* 83:9129–9133 (Dec. 1986).
Masuko et al "A Murine Monoclonal Antibody That Recognizes an Extracellular . . ." *Jpn. J. Cancer Res.* 80:10–14 (Jan. 1989).
Kraus et al "Overexpression of the EGF Receptor–Related Proto–Oncogene erbB–2 . . ." *EMBO J.* 6(3):605–610 (1986).
Hudziak et al., "Increased Expression of the Putative Growth Factor Receptor p185$^{HER2}$ . . . " *PNAS* 84:7159–7163 (Oct. 1987).* van de Vijver et al, "Amplification of the neu(c–erbB–2) Oncogene . . . " *Mol. Cell. Biol.* 7(5):2019–2023 (May 1987).*
Yokota et al, "Genetic Alterations of the c–erbB–2 Oncogene . . . " *Oncogene* 2:283–287 (1988).*
Zhou et al, "Association of Multiple Copies of the c–erbB–2 Oncogene . . . " *Cancer Res.* 47:6123–6125 (Nov. 1987).*
Yamamoto et al, "Similarity of Protein Encoded by the Human c–erb–B–2 Gene to Epidermal Growth Factor Receptor", *Nature* 319:230–234 (Jan. 1986).*
Coussens et al, "Tyrosine Kinase Receptor with Extensive Homology to EGF Receptor . . . ", *Science* 230:1132–1139 (Dec. 1985).*
Weber et al, "Medium–Scale Ligand–Affinity Purification . . . " *J. Chromat.* 431:55–63 (1988).*
Semba et al, "A v–erbB–related Protooncogene, c–erbB–2 . . . " *PNAS* 82:6497–6501 (Oct. 1985).*
Akiyama et al., "The product of the human c–erbB–2 Gene: a 185–Kilodalton Glycoprotein with tyrosine Kinase Activity" *Science* 232:1644–1646 (1986).
Bargmann et al., "The neu oncogene encodes an epidermal growth factor receptor–related protein" *Nature* 319:226–230 (1986).
Bernards et al., "Effective tumor immunotherapy directed against an oncogene–encoded product using a vaccinia virus vector" *Proc. Natl. Acad. Sci. USA* 84:6854–6858 (1987).
Coussens et al., "Tyrosine Kinase Receptor with Extensive Homology to EGF Receptor Shares Chromosomal Location with neu Oncogene" *Science* 230:1132–1139 (1985).
Drebin et al., "Down–Modulation of an Oncogene Protein Product an Reversion of the Transformed Phenotype by Monoclonal Antobodies" *Cell* 41(3):695–706 (1985).
Drebin et al., "Inhibition of tumor growth by a monoclonal antibody reactive with an oncogene–encoded tumor antigen" *Proc. Natl. Acad. Sci.* 83:9129–9133 (1986).
Drebin et al., "Monoclonal antibodies reactive with distinct domains of the neu oncogene–encoded p185 molecule exert synergistic anti–tumor effects in vivo" *Oncogene* 2:273–277 (1988).
Drebin et al., "Monoclonal antibodies specific for the neu oncogene product directly mediate anti–tumor effects in vivo" *Oncogene* 2(4):387–394 (1988).
Fendly et al., "The Extracellular Domain of HER2/neu Is a Potential Immunogen for Active Specific Immunotherapy of Breast Cancer" *Journal of Biological Response Modifiers* 9:449–455 (1990).

(List continued on next page.)

*Primary Examiner*—Gary L. Kunz

(57) ABSTRACT

An extracellular portion of the HER2 molecule, essentially free of transmembrane and cytoplasmic portions, which is antigenic in animals. Isolated DNA encoding the extracellular portion; an expression vector containing the isolated DNA; and a cell containing the expression vector. A process for producing the extracellular domain. A vaccine containing the extracellular domain.

16 Claims, 13 Drawing Sheets

OTHER PUBLICATIONS

Fendly et al., "Successful Immunization of Rhesus Monkeys with Extracellular Domain of p185$^{HER2}$:A Potential Approach to Human Breast Cancer" *Vaccine Research* 2(3):129–139 (1993).

Graham et al., "A New Technique for the Assay of Infectivity of Human Adenovirus 5 DNA" *Virology* 52:456–467 (1973).

Hopp et al., "Prediction of protein antigenic determinants from amino acid sequences" *Proc. Natl. Acad. Sci. USA* 78(6):3824–3828 (1981).

Hudziak et al., "Amplified Expression of the HER2/ERBB2 Oncogene Induces Resistance to Tumor Necrosis Factor α in NIH 3T3 Cells" *Proc. Natl. Acad. Sci. USA* 85:5102–5106 (1988).

Hudziak et al., "Increased expression of the putative growth factor receptor p185$^{HER2}$ causes transformation and tumorigenesis of NIH 3T3 cells" *Proc. Natl. Acad. Sci.* 84:7159–7163 (1987).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165–1172 (1989).

Kane et al., "Formation of recombinant protein inclusion bodies in *Escherichia coli*" *Tibtech* 6:95–101 (1988).

Kaufman et al., "Amplification and Expression of Sequences Cotransfected with a Modular Dihydrofolate Reductase Complementary DNA Gene" *J. Mol. Biol.* 159:601–621 (1982).

King et al., "Amplification of a Novel v–erbB–Related Gene in a Human Mammary Carcinoma" *Science* 229:974–976 (1985).

Kraus et al., "Overexpression of the EGF receptor–related proto–oncogene erbB2 in human mammary tumor cell lines by different molecular mechanisms" *EMBO Journal* 6(3):605–610 (1987).

Langton et al., "An antigen immunologically related to the external domain of gp185 is shed from nude mouse tumors overexpressing the c–erbB–2 (HER–2/neu) oncogene" *Cancer Research* 51:2593–2598 (1991).

Lin et al., "A soluble protein related to the HER–2 proto–oncogene product is released from human breast carcinoma cells" *Oncogene* 6:639–643 (1991).

Margalit et al., "Prediction of Immunodominant Helper T Cell Antigenic Sites from the Primary Sequence" *J. Immunol.* 138(7):2213–2229 (1987).

Masuko et al., "A murine monoclonal antibody that recognizes an extracellular domain of the human c–erbB–2 protooncogene product" *Jpn J. Cancer Res.* 80:10–14 (1989).

Padhy et al., "Identification of a Phosphoprotein Specifically Induced by the Transforming DNA of Rat Neuroblastomas" *Cell* 28:865–871 (1982).

Plowman et al., "Ligand–specific activation of HER4/p180$^{erbB4}$, a fourth member of the epidermal growth factor receptor family" *Proc. Natl. Acad. Sci. USA* 90:1746–1750 (1993).

Schecter et al., "The new oncogene: an erb–B–related gene encoding a 185,000–Mr tumour antigen" *Nature* 312:513–516 (1984).

Schein, Catherine H., "Production of soluble recombinant proteins in bacteria" *Bio/Technology* 7:1141–1149 (1989).

Semba et al., "A v–erbB–related protooncogene c–erbB–2, is distinct from the c–erb–B–1/epidermal growth factor–receptor gene and is amplified in a human salivary gland adenocarcinoma" *Proc. Natl. Acad. Sci. USA* 82:6497–6501 (1985).

Shepard et al., "P185HER2 Monoclonal Antibody has Anti Proliferative Effects in vitro and sensitizes human breast tumor cells to tumor necrosis factor" *J. Cell Biochem.* (Abstract D253) pp. 42 (1989).

Slamon et al., "Human Breast Cancer: Correlation of Relapse and Survival with Amplification of the HER–2/neu Oncogene" *Science* 235:177–182 (1987).

Sliwkowski et al., "Coexpression of erbB2 and erbB3 proteins reconstitutes a high affinity receptor for heregulin" *Journal of Biological Chemistry* 269(20):14661–14665 (1994).

Van de Vijver et al., "Amplification of the neu (c–erbB–2) Oncogene in Human Mammary Tumors Is Relatively Frequent and Is Often Accompanied by Amplification of the Linked c–erbA Oncogene" *Molecular & Cellular Biology* 7(5):2019–2023 (1987).

Weber et al., "Medium–scale ligand–affinity purification of two soluble forms of human interleukin–2 receptor" *J. Chromatography* 431:55–63 (1988).

Yamamoto et al., "Similarity of protein encoded by the human c–erb–B 2 gene to epidermal growth factor receptor" *Nature* 319:230–34 (1986).

Yanisch–Perron et al., "Improved M13 phage cloning vectors and host strains: nucleotide sequences of the M13mp18 and pUC19 vectors" *Gene* 33:103–119 (1985).

Yarden et al., "Epidermal Growth Factor Induces Rapid, Reversible Aggregation of the Purified Epidermal Growth Factor Receptor" *Biochemistry* 26:1443–1451 (1987).

Yarden et al., "Growth Factor Receptor Tyrosine Kinases" *Ann. Rev. Biochem.* 57:443–478 (1988).

Yarden et al., "Molecular Analysis of Signal Transduction by Growth Factors" *Biochemistry* 27(9):3113–3119 (1988).

Yokota et al., "Genetic alterations of the c–erbB–2 oncogene occur frequently in tubular adenocarcinoma of the stomach and are often accompanied by amplification of the v–erbA homologue" *Oncogene* 2:283–287 (1988).

Zhou et al., "Association of Multiple Copies of the c–erbB–2 Oncogene with Spread of Breast Cancer" *Cancer Research* 47:6123–6125 (1987).

Basu et al., "Inhibition of Tyrosine Kinase Activity of the Epidermal Growth Factor (EGF) Receptor by a Truncated Receptor Form that Binds to EGF: Role for Interrecptor Interaction in Kinase Regulation" *Molecular & Cellular Biology* 9(2):671–677 (Feb. 1988).

Capon et al., "Designing CD4 Immunoadhesins for AIDS Therapy" *Nature* 337:525–531 (Feb. 9, 1989).

Disis et al., "Existent T–Cell and Antibody Immunity to HER–2/neu Protein in Patients with Breast Cancer" *Cancer Research* 54:16–20 (Jan. 1, 1994).

Drebin et al., "Monoclonal Antibodies Identify a Cell–surface Antigen Associated with an Activated Cellular Oncogene" *Nature* 312:545–548 (Dec. 6, 1984).

Duan et al., "A Functional Soluble Extracellular Region of the Platelet–derived Growth Factor (PDGF) β–Receptor Antagonized PDGF–stimulated Responses" *Journal of Biological Chemistry* 266(1):413–418 (Jan. 5, 1991).

Ezzell, C., "Cancer 'Vaccines': An Idea Whose Time Has Come?" *Journal of NIH Research* 7:46–49 (Jan. 1995).

Hoover et al., "Prospectively Randomized Trial of Adjuvant Active–specific Immunotherapy for Human Colorectal Cancer" *Cancer* 55(6):1236–1243 (Mar. 15, 1985).

Mitchell et al., "Active Specific Immunotherapy for Melanoma: Phase I Trial of Allogenic Lysates and a Novel Adjuvant" *Cancer Research* 48:5883–5893 (Oct. 15, 1988).

Tal et al., "Sporadic Amplification of the Her2/neu Protooncogene in Adenocarinomas of Various Tissues" *Cancer Research* 48:1517–1520 (Mar. 15, 1988).

Weber et al., "Production of an Epidermal Growth Factor Receptor–Related Protein" *Science* 224:294–297 (Apr. 20, 1984).

* cited by examiner

POTENTIAL T-CELL EPITOPES IN THE HER2 EXTRACELLULAR DOMAIN

```
  1                                          10                                          20
SER THR GLN VAL CYS THR GLY THR ASP MET LYS LEU ARG LEU PRO ALA SER PRO GLU THR
AGC ACC CAA GUG UGC ACC GGC ACA GAC AUG AAG CUC CGG CUC CCU GCC AGU CCC GAG ACC 30                                          40
HIS LEU ASP MET LEU ARG HIS LEU TYR GLN GLY CYS GLN VAL VAL GLN GLY ASN LEU GLU
CAC CUG GAC AUG CUC CGC CAC CUC UAC CAG GGC UGC CAG GUG GUG CAG GGA AAC CUG GAA 50                                          60
LEU THR TYR LEU PRO THR ASN ALA SER LEU SER PHE LEU GLN ASP ILE GLN GLU VAL GLN
CUC ACC UAC CUG CCC ACC AAU GCC AGC CUG UCC UUC CUG CAG GAU AUC CAG GAG GUG CAG 70                                          80
GLY TYR VAL LEU ILE ALA HIS ASN GLN VAL ARG GLN VAL PRO LEU GLN ARG LEU ARG ILE
GGC UAC GUG CUC AUC GCU CAC AAC CAA GUG AGG CAG GUC CCA CUG CAG AGG CUG CGG AUU 90                                         100
VAL ARG GLY THR GLN LEU PHE GLU ASP ASN TYR ALA LEU ALA VAL LEU ASP ASN GLY ASP
GUG CGA GGC ACC CAG CUC UUU GAG GAC AAC UAU GCC CUG GCC GUG CUA GAC AAU GGA GAC 110                                         120
PRO LEU ASN ASN THR THR PRO VAL THR GLY ALA SER PRO GLY GLY LEU ARG GLU LEU GLN
CCG CUG AAC AAU ACC ACC CCU GUC ACA GGG GCC UCC CCA GGA GGC CUG CGG GAG CUG CAG 130                                         140
LEU ARG SER LEU THR GLU ILE LEU LYS GLY GLY VAL LEU ILE GLN ARG ASN PRO GLN LEU
CUU CGA AGC CUC ACA GAG AUC UUG AAA GGA GGG GUC UUG AUC CAG CGG AAC CCC CAG CUC 150                                         160
CYS TYR GLN ASP THR ILE LEU TRP LYS ASP ILE PHE HIS LYS ASN ASN GLN LEU ALA LEU
UGC UAC CAG GAC ACG AUU UUG UGG AAG GAC AUC UUC CAC AAG AAC AAC CAG CUG GCU CUC
```

FIG. 13A

```
                                    170                     180
THR LEU ILE ASP THR ASN ARG SER ARG ALA CYS HIS PRO CYS SER PRO MET CYS LYS GLY
ACA CUG AUA GAC ACC AAC CGC UCU CGG GCC UGC CAC CCC UGU UCU CCG AUG UGU AAG GGC
                                        190                     200
SER ARG CYS TRP GLY GLU SER SER GLU GLU ASP CYS GLN SER LEU THR ARG THR VAL CYS ALA
UCC CGC UGC UGG GGA GAG AGU UCU GAG GAG GAU UGU CAG AGC CUG ACG CGC ACU GUC UGU GCC
                                        210                     220
GLY GLY CYS ALA ARG CYS LYS GLY PRO LEU PRO THR ASP CYS CYS HIS GLU GLN CYS ALA
GGU GGC UGU GCC CGC UGC AAG GGG CCA CUG CCC ACU GAC UGC UGC CAU GAG CAG UGU GCU
                                        230                     240
ALA GLY CYS THR GLY PRO LYS HIS SER ASP CYS LEU ALA CYS LEU HIS PHE ASN HIS SER
GCC GGC UGC ACG GGC CCC AAG CAC UCU GAC UGC CUG GCC UGC CUC CAC UUC AAC CAC AGU
                                        250                     260
GLY ILE CYS GLU LEU HIS CYS PRO ALA LEU VAL THR TYR ASN THR ASP THR PHE GLU SER
GGC AUC UGU GAG CUG CAC UGC CCA GCC CUG GUC ACC UAC AAC ACA GAC ACG UUU GAG UCC
                                        270                     280
MET PRO ASN PRO GLU GLY ARG TYR THR PHE GLY ALA SER CYS VAL THR ALA CYS PRO TYR
AUG CCC AAU CCC GAG GGC CGG UAU ACA UUC GGC GCC AGC UGU GUG ACU GCC UGU CCC UAC
                                        290                     300
ASN TYR LEU SER THR ASP VAL GLY SER CYS THR LEU VAL CYS PRO LEU HIS ASN GLN GLU
AAC UAC CUU UCU ACG GAC GUG GGA UCC UGC ACC CUC GUC UGC CCC CUG CAC AAC CAA GAG
                                        310                     320
VAL THR ALA GLU ASP GLY THR GLN ARG CYS GLU LYS CYS SER LYS PRO CYS ALA ARG VAL
GUG ACA GCA GAG GAU GGA ACA CAG CGG UGU GAG AAG UGC AGC AAG CCC UGU GCC CGA GUG
                                        330                     340
CYS TYR GLY LEU GLY MET GLU HIS LEU ARG GLU VAL ARG ALA VAL THR SER ALA ASN ILE
UGC UAU GGU CUG GGC AUG GAG CAC UUG CGA GAG GUG AGG GCA GUU ACC AGU GCC AAU AUC
```

FIG. 13B

```
                                                  350                                                   360
GLN GLU PHE ALA GLY CYS LYS LYS ILE PHE GLY SER LEU ALA PHE LEU PRO GLU SER PHE
CAG GAG UUU GCU GGC UGC AAG AAG AUC UUU GGG AGC CUG GCA UUU CUG CCG GAG AGC UUU 370                                                   380
ASP GLY ASP PRO ALA SER ASN THR ALA PRO LEU GLN PRO GLU GLN LEU GLN VAL PHE GLU
GAU GGG GAC CCA GCC UCC AAC ACU GCC CCG CUC CAG CCA GAG CAG CUC CAA GUG UUU GAG 390                                                   400
THR LEU GLU GLU ILE THR GLY TYR LEU TYR ILE SER ALA TRP PRO ASP SER LEU PRO ASP
ACU CUG GAA GAG AUC ACA GGU UAC CUA UAC AUC UCA GCA UGG CCG GAC AGC CUG CCU GAC 410                                                   420
LEU SER VAL PHE GLN ASN LEU GLN VAL ILE ARG GLY ARG ILE LEU HIS ASN GLY ALA TYR
CUC AGC GUC UUC CAG AAC CUG CAA GUA AUC CGG GGA CGA AUU CUG CAC AAU GGC GCC UAC 430                                                   440
SER LEU THR LEU GLN GLY LEU GLY ILE SER TRP LEU GLY LEU ARG SER LEU ARG GLU LEU
UCG CUG ACC CUG CAA GGG CUG GGC AUC AGC UGG CUG GGG CUG CGC UCA CUG AGG GAA CUG 450                                                   460
GLY SER GLY LEU ALA LEU ILE HIS HIS ASN THR HIS LEU CYS PHE VAL HIS THR VAL PRO
GGC AGU GGA CUG GCC CUC AUC CAC CAU AAC ACC CAC CUC UGC UUC GUG CAC ACG GUG CCC 470                                                   480
TRP ASP GLN LEU PHE ARG ASN PRO HIS GLN ALA LEU LEU HIS THR ALA ASN ARG PRO GLU
UGG GAC CAG CUC UUU CGG AAC CCG CAC CAA GCU CUG CUC CAC ACU GCC AAC CGG CCA GAG 490                                                   500
ASP GLU CYS VAL GLY GLU GLY LEU ALA CYS HIS GLN LEU CYS ALA ARG GLY HIS CYS TRP
GAC GAG UGU GUG GGC GAG GGC CUG GCC UGC CAC CAG CUG UGC GCC CGA GGG CAC UGC UGG 510                                                   520
GLY PRO GLY PRO THR GLN CYS VAL ASN CYS SER GLN PHE LEU ARG GLY GLN GLU CYS VAL
GGU CCA GGG CCC ACC CAG UGU GUC AAC UGC AGC CAG UUC CUU CGG GGC CAG GAG UGC GUG
```

FIG. 13C

```
GLU GLU CYS ARG VAL LEU GLN GLY LEU  530 PRO ARG GLU TYR VAL ASN ALA ARG HIS CYS 540 LEU
GAG GAA UGC CGA GUA CUG CAG GGG CUC      CCC AGG GAG UAU GUG AAU GCC AGG CAC UGU     UUG

PRO CYS HIS PRO GLU CYS GLN PRO         550 ASN GLY SER VAL THR CYS PHE GLY PRO GLU 560 ALA
CCG UGC CAC CCU GAG UGU CAG CAG             AAU GGC UCA GUG ACC UGU UUU GGA CCG GAG     GCU

ASP GLN CYS VAL ALA CYS ALA HIS TYR     570 LYS ASP PRO PRO PHE CYS VAL ALA ARG CYS 580 PRO
GAC CAG UGU GUG GCC UGC GCC CAC UAU         AAG GAC CCU CCC UUC UGC GUG GCC CGC UGC     CCC

SER GLY VAL LYS PRO ASP LEU SER TYR     590 MET PRO ILE TRP LYS PHE PRO ASP GLU GLY 600 GLY
AGC GGU GUG AAA CCU GAC CUC UCC UAC         AUG CCC AUC UGG AAG UUU CCA GAU GAG GAG     GGC

ALA CYS GLN PRO CYS PRO ILE ASN CYS     610 THR HIS SER CYS VAL ASP LEU ASP ASP LYS 620 GLY
GCA UGC CAG CCU UGC CCC AUC AAC UGC         ACC CAC UCC UGU GUG GAC CUG GAU GAC AAG     GGC

624 CYS PRO ALA GLU
    UCC CCC GCC GAG
```

FIG. 13D

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 624 amino acids
        (B) TYPE: Amino Acid
        (D) TOPOLOGY: Linear (xi) SEQUENCE DESCRIPTION: SEQ ID NO:1:

```
Ser Thr Gln Val Cys Thr Gly Thr Asp Met Lys Leu Arg Leu Pro
 1               5                  10                  15

Ala Ser Pro Glu Thr His Leu Asp Met Leu Arg His Leu Tyr Gln
                20                  25                  30

Gly Cys Gln Val Val Gln Gly Asn Leu Glu Leu Thr Tyr Leu Pro
                35                  40                  45

Thr Asn Ala Ser Leu Ser Phe Leu Gln Asp Ile Gln Glu Val Gln
                50                  55                  60

Gly Tyr Val Leu Ile Ala His Asn Gln Val Arg Gln Val Pro Leu
                65                  70                  75

Gln Arg Leu Arg Ile Val Arg Gly Thr Gln Leu Phe Glu Asp Asn
                80                  85                  90

Tyr Ala Leu Ala Val Leu Asp Asn Gly Asp Pro Leu Asn Asn Thr
                95                  100                 105

Thr Pro Val Thr Gly Ala Ser Pro Gly Gly Leu Arg Glu Leu Gln
                110                 115                 120

Leu Arg Ser Leu Thr Glu Ile Leu Lys Gly Gly Val Leu Ile Gln
                125                 130                 135

Arg Asn Pro Gln Leu Cys Tyr Gln Asp Thr Ile Leu Trp Lys Asp
                140                 145                 150

Ile Phe His Lys Asn Asn Gln Leu Ala Leu Thr Leu Ile Asp Thr
                155                 160                 165

Asn Arg Ser Arg Ala Cys His Pro Cys Ser Pro Met Cys Lys Gly
                170                 175                 180

Ser Arg Cys Trp Gly Glu Ser Ser Glu Asp Cys Gln Ser Leu Thr
                185                 190                 195

Arg Thr Val Cys Ala Gly Gly Cys Ala Arg Cys Lys Gly Pro Leu
                200                 205                 210
```

-continued

```
Pro Thr Asp Cys Cys His Glu Gln Cys Ala Ala Gly Cys Thr Gly
            215                 220                 225
Pro Lys His Ser Asp Cys Leu Ala Cys Leu His Phe Asn His Ser
            230                 235                 240
Gly Ile Cys Glu Leu His Cys Pro Ala Leu Val Thr Tyr Asn Thr
            245                 250                 255
Asp Thr Phe Glu Ser Met Pro Asn Pro Glu Gly Arg Tyr Thr Phe
            260                 265                 270
Gly Ala Ser Cys Val Thr Ala Cys Pro Tyr Asn Tyr Leu Ser Thr
            275                 280                 285
Asp Val Gly Ser Cys Thr Leu Val Cys Pro Leu His Asn Gln Glu
            290                 295                 300
Val Thr Ala Glu Asp Gly Thr Gln Arg Cys Glu Lys Cys Ser Lys
            305                 310                 315
Pro Cys Ala Arg Val Cys Tyr Gly Leu Gly Met Glu His Leu Arg
            320                 325                 330
Glu Val Arg Ala Val Thr Ser Ala Asn Ile Gln Glu Phe Ala Gly
            335                 340                 345
Cys Lys Lys Ile Phe Gly Ser Leu Ala Phe Leu Pro Glu Ser Phe
            350                 355                 360
Asp Gly Asp Pro Ala Ser Asn Thr Ala Pro Leu Gln Pro Glu Gln
            365                 370                 375
Leu Gln Val Phe Glu Thr Leu Glu Glu Ile Thr Glu Tyr Leu Tyr
            380                 385                 390
Ile Ser Ala Trp Pro Asp Ser Leu Pro Asp Leu Ser Val Phe Gln
            395                 400                 405
Asn Leu Gln Val Ile Arg Gly Arg Ile Leu His Asn Gly Ala Tyr
            410                 415                 420
Ser Leu Thr Leu Gln Gly Leu Gly Ile Ser Trp Leu Gly Leu Arg
            425                 430                 435
Ser Leu Arg Glu Leu Gly Ser Gly Leu Ala Leu Ile His His Asn
            440                 445                 450
Thr His Leu Cys Phe Val His Thr Val Pro Trp Asp Gln Leu Phe
            455                 460                 465
Arg Asn Pro His Gln Ala Leu Leu His Thr Ala Asn Arg Pro Glu
            470                 475                 480
Asp Glu Cys Val Gly Glu Gly Leu Ala Cys His Gln Leu Cys Ala
            485                 490                 495
Arg Gly His Cys Trp Gly Pro Gly Pro Thr Gln Cys Val Asn Cys
            500                 505                 510
Ser Gln Phe Leu Arg Gly Gln Glu Cys Val Glu Glu Cys Arg Val
            515                 520                 525
Leu Gln Gly Leu Pro Arg Glu Tyr Val Asn Ala Arg His Cys Leu
            530                 535                 540
Pro Cys His Pro Glu Cys Gln Pro Gln Asn Gly Ser Val Thr Cys
            545                 550                 555
Phe Gly Pro Glu Ala Asp Gln Cys Val Ala Cys Ala His Tyr Lys
            560                 565                 570
Asp Pro Pro Phe Cys Val Ala Arg Cys Pro Ser Gly Val Lys Pro
            575                 580                 585
Asp Leu Ser Tyr Met Pro Ile Trp Lys Phe Pro Asp Glu Glu Gly
            590                 595                 600
Ala Cys Gln Pro Cys Pro Ile Asn Cys Thr His Ser Cys Val Asp
```

-continued

```
                605                 610                 615
Leu Asp Asp Lys Gly Cys Pro Ala Glu
                    620             624

(2) INFORMATION FOR SEQ ID NO:2:

(i) SEQUENCE CHARACTERISTICS:
        (A) LENGTH: 1872 nucleotides
        (B) TYPE: Nucleic Acid
        (C) STRANDEDNESS: Single
        (D) TOPOLOGY: Linear (xi) SEQUENCE DESCRIPTION: SEQ ID NO:2:

AGCACCCAAG UGUGCACCGG CACAGACAUG AAGCUGCGGC UCCCUGCCAG         50

UCCCGAGACC CACCUGGACA UGCUCCGCCA CCUCUACCAG GGCUGCCAGG        100

UGGUGCAGGG AAACCUGGAA CUCACCUACC UGCCCACCAA UGCCAGCCUG        150

UCCUUCCUGC AGGAUAUCCA GGAGGUGCAG GGCUACGUGC UCAUCGCUCA        200

CAACCAAGUG AGGCAGGUCC CACUGCAGAG GCUGCGGAUU GUGCGAGGCA        250

CCCAGCUCUU UGAGGACAAC UAUGCCCUGG CCGUGCUAGA CAAUGGAGAC        300

CCGCUGAACA AUACCACCCC UGUCACAGGG GCCUCCCCAG GAGGCCUGCG        350

GGAGCUGCAG CUUCGAAGCC UCACAGAGAU CUUGAAAGGA GGGGUCUUGA        400

UCCAGCGGAA CCCCCAGCUC UGCUACCAGG ACACGAUUUU GUGGAAGGAC        450

AUCUUCCACA AGAACAACCA GCUGGCUCUC ACACUGAUAG ACACCAACCG        500

CUCUCGGGCC UGCCACCCCU GUUCUCCGAU GUGUAAGGGC UCCCGCUGCU        550

GGGGAGAGAG UUCUGAGGAU UGUCAGAGCC UGACGCGCAC UGUCUGUGCC        600

GGUGGCUGUG CCCGCUGCAA GGGGCCACUG CCCACUGACU GCUGCCAUGA        650

GCAGUGUGCU GCCGGCUGCA CGGGCCCCAA GCACUCUGAC UGCCUGGCCU        700

GCCUCCACUU CAACCACAGU GGCAUCUGUG AGCUGCACUG CCCAGCCCUG        750

GUCACCUACA ACACAGACAC GUUUGAGUCC AUGCCCAAUC CGAGGGCCG         800

GUAUACAUUC GGCGCCAGCU GUGUGACUGC CUGUCCCUAC AACUACCUUU        850

CUACGGACGU GGGAUCCUGC ACCCUCGUCU GCCCCCUGCA CAACCAAGAG        900

GUGACAGCAG AGGAUGGAAC ACAGCGGUGU GAGAAGUGCA GCAAGCCCUG        950

UGCCCGAGUG UGCUAUGGUC UGGGCAUGGA GCACUUGCGA GAGGUGAGGG       1000

CAGUUACCAG UGCCAAUAUC CAGGAGUUUG CUGGCUGCAA GAAGAUCUUU       1050

GGGAGCCUGG CAUUUCUGCC GGAGAGCUUU GAUGGGGACC CAGCCUCCAA       1100

CACUGCCCCG CUCCAGCCAG AGCAGCUCCA AGUGUUUGAG ACUCUGGAAG       1150

AGAUCACAGG UUACCUAUAC AUCUCAGCAU GGCCGGACAG CCUGCCUGAC       1200

CUCAGCGUCU UCCAGAACCU GCAAGUAAUC CGGGGACGAA UUCUGCACAA       1250

UGGCGCCUAC UCGCUGACCC UGCAAGGGCU GGGCAUCAGC UGGCUGGGGC       1300

UGCGCUCACU GAGGGAACUG GGCAGUGGAC UGGCCCUCAU CCACCAUAAC       1350

ACCCACCUCU GCUUCGUGCA CACGGUGCCC UGGGACCAGC UCUUUCGGAA       1400

CCCGCACCAA GCUCUGCUCC ACACUGCCAA CCGGCCAGAG GACGAGUGUG       1450

UGGGCGAGGG CCUGGCCUGC CACCAGCUGU GCGCCCGAGG GCACUGCUGG       1500

GGUCCAGGGC CCACCCAGUG UGUCAACUGC AGCCAGUUCC UUCGGGGCCA       1550

GGAGUGCGUG GAGGAAUGCC GAGUACUGCA GGGGCUCCCC AGGGAGUAUG       1600
```

-continued

| | | | | |
|---|---|---|---|---|
| UGAAUGCCAG | GCACUGUUUG | CCGUGCCACC | CUGAGUGUCA | GCCCCAGAAU | 1650 |
| GGCUCAGUGA | CCUGUUUUGG | ACCGGAGGCU | GACCAGUGUG | UGGCCUGUGC | 1700 |
| CCACUAUAAG | GACCCUCCCU | UCUGCGUGGC | CCGCUGCCCC | AGCGGUGUGA | 1750 |
| AACCUGACCU | CUCCUACAUG | CCCAUCUGGA | AGUUUCCAGA | UGAGGAGGGC | 1800 |
| GCAUGCCAGC | CUUGCCCCAU | CAACUGCACC | CACUCCUGUG | UGGACCUGGA | 1850 |
| UGACAAGGGC | UCCCCCGCCG | AG | | | 1872 |

HER2 EXTRACELLULAR DOMAIN

This is a divisional of application Ser. No. 08/355,460 filed on Dec. 13, 1994, now abandoned, which application is a continuation of Ser. No. 08/048,346 filed Apr. 15, 1993, now abandoned, which application is a continuation of Ser. No. 07/354,319 filed May 19, 1989, now abandoned, which application(s) is(are) incorporated herein by reference and to which application(s) priority is claimed under 35 USC § 120.

BACKGROUND OF THE INVENTION

1. Field of the Invention

The present invention is generally directed to the extracellular domain of $p185^{HER2}$, a receptor-like protein which is encoded by the human homolog of the rat neu oncogene.

More specifically, the present invention is directed to a form of the extracellular domain which is essentially free of transmembrane and cytoplasmic domains, to the DNA encoding this form, and to a process for producing this form of the extracellular domain in a host cell.

2. Description of Background and Relevant Materials

Human epidermal growth factor receptor 2 (HER2, also known as NGL and human c-erbB-2, or ERBB2), is the human homolog of the rat proto-oncogene neu. HER2 encodes a 1,255 amino acid tyrosine kinase receptor-like glycoprotein with homology to the human epidermal growth factor receptor. Although no ligand binding to this probable growth factor receptor has yet been isolated, the HER2 gene product, $p185^{HER2}$, has the structural and functional properties of subclass I growth factor receptors (Yarden et al., *Ann. Rev. Biochem.*, 57:443–478 (1988); Yarden et al., *Biochem.*, 27:3113–3119 (1988)).

The receptor tyrosine kinases all have the same general structural motif; an extracellular domain that binds ligand, and an intracellular tyrosine kinase domain that is necessary for signal transduction, or in aberrant cases, for transformation. These 2 domains are connected by a single stretch of approximately 20 mostly hydrophobic amino acids, called the transmembrane spanning sequence. This sequence is thought to play a role in transferring the signal generated by ligand binding from the outside of the cell to the inside. It has also been suggested to play a role in the proper positioning of the receptor in the plasma membrane.

Consistent with this general structure, the $p185^{HER2}$ glycoprotein, which is located on the cell surface, may be divided into three principle portions: an extracellular domain, or ECD (also known as XCD); a transmembrane spanning sequence; and a cytoplasmic, intracellular tyrosine kinase domain. While it is presumed that the extracellular domain is a ligand receptor, as stated above the corresponding ligand has not yet been identified.

The HER2 gene is of particular interest because its amplification has been correlated with certain types of cancer. Amplification of the HER2 gene has been found in human salivary gland and gastric tumor-derived cell lines, gastric and colon adenocarcinomas, and mammary gland adenocarcinomas. Semba et al., *Proc. Natl. Acad. Sci. USA*, 82:6497–6501 (1985); Yokota et al., *Oncogene*, 2:283–287 (1988); Zhou et al., *Cancer Res.*, 47:6123–6125 (1987); King et al., *Science*, 229:974–976 (1985); Kraus et al., *EMBO J.*, 6:605–610 (1987); van de Vijver et al., *Mol. Cell. Biol.*, 7:2019–2023 (1987); Yamamoto et al., *Nature*, 319:230–234 (1986).

Gene transfer experiments have shown that overexpression of HER2 will transform NIH 3T3 cells and also cause an increase in resistance to the toxic macrophage cytokine tumor necrosis factor. Hudziak et al., "Amplified Expression of the HER2/ERBB2 Oncogene Induces Resistance to Tumor Necrosis Factor Alpha in NIH 3T3 Cells", *Proc. Natl. Acad. Sci. USA* 85, 5102–5106 (1988).

Because amplification of the HER2 gene results in greatly increased numbers of the $p185^{HER2}$ protein residing on the surfaces of affected cells, there may be an interrelationship between increased amounts of $p185^{HER2}$ extracellular domain on the surfaces of affected cells and the resistance of these cells to treatment. It would therefore be highly desirable to be able to manipulate the $p185^{HER2}$ extracellular domain in order to investigate several possibilities for the treatment of conditions associated with amplification of the HER2 gene. These therapeutic modes relate not only to the extracellular domain, but also to the putative ligand, which it should be possible to isolate and characterize using the purified $p185^{HER2}$ extracellular domain.

SUMMARY OF THE INVENTION

The present invention is accordingly directed to an extracellular portion of the HER2 molecule containing at least 9 amino acids, and/or containing an immune epitope, which is essentially free of transmembrane and intracellular portions of the HER2 molecule. The extracellular portion may be substantially pure, or at least about 99% pure, and may extend to the entire extracellular portion of the HER2 molecule. Moreover, the extracellular portion may be antigenic in animals, and may be conjugated with a peptide having immunogenic properties; this peptide may contain an immune epitope.

In another embodiment, the present invention is directed to isolated DNA encoding the extracellular portion of the HER2 molecule. This isolated DNA terminates upstream of the DNA portion encoding the transmembrane domain of the HER2 molecule. The termination may occur at least 1 base pair upstream of the portion encoding the transmembrane domain of the HER2 molecule, and preferably occurs about 24 base pairs upstream of this portion.

The isolated DNA of the present invention encodes a sequence of at least 9 amino acids of the extracellular portion, and none of the transmembrane or intracellular portions of the HER2 molecule.

In a further embodiment, the present invention contemplates an expression vector, such as a plasmid or virus, containing the isolated DNA as described above, as well as a cell containing the expression vector. This cell may be eukaryotic or prokaryotic.

The present invention also extends to a process for producing an extracellular portion of the HER2 molecule, which includes the steps of ligating the isolated DNA as described above into an expression vector capable of expressing the isolated DNA in a suitable host; transforming the host with the expression vector; culturing the host under conditions suitable for expression of the isolated DNA and production of the extracellular portion; and isolating the extracellular portion from the host. The host cell may be a prokaryote, such as a bacterium, or a eukaryote.

In a yet further embodiment, the present invention extends to a vaccine comprising the extracellular portion of the HER2 molecule, which may be combined with suitable adjuvants.

BRIEF DESCRIPTION OF FIGURES

FIG. 13. The predicted amino acid sequence of the HER2 extracellular domain (SEQ ID NO:1), with the corresponding nucleic acid sequence (SEQ ID NO:2). The boxed sequences show potential T-cell epitopes, using the algorithm developed by Margolit et al., J. Immunol. 138:2213–2229(4) (1987).

DETAILED DESCRIPTION

It was initially hypothesized that removal of the transmembrane spanning sequence would yield a protein which would be secreted from the cell. As previously indicated, the transmembrane spanning sequence is principally composed of hydrophobic amino acids, which effectively anchor the protein in the cell membrane. Removal of this sequence would therefore be expected to permit passage of the protein through the membrane.

Figure 1A:
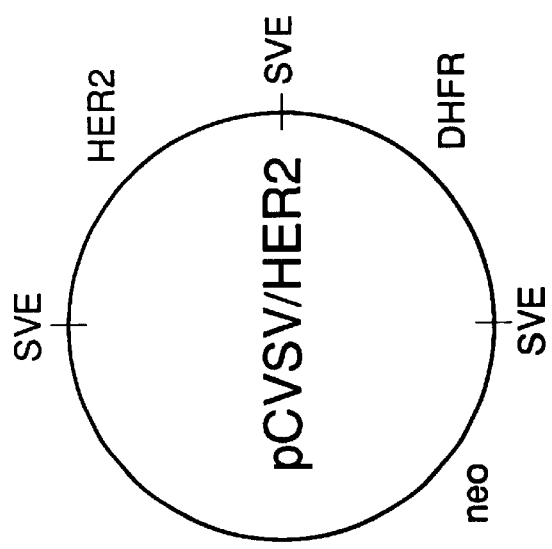
FIGS. 1A and 1B HER2 expression vector and full-length and mutant HER2 proteins. The HER2 expression vector contained eukaryotic transcriptional units for the mouse dihydrofolate reductase (DHFR) cDNA and the bacterial neomycin phosphotransferase (neo) gene, both under SV40 early promoter control. Transcription of the full-length HER2 cDNA was also driven by the early SV40 promoter. The full-length HER2 protein contains an extracellular domain with two cysteine-rich clusters (hatched rectangle), separated by the transmembrane-spanning region (filled rectangle) from the intracellular tyrosine kinase domain (open rectangle). The mutant protein p185$^{HER2\Delta TM}$ has a deletion of 28 amino acids, including the transmembrane-spanning region. The truncated p185$^{HER2XCD}$ protein contains all N-terminal sequences up to 8 amino acids before the transmembrane-spanning region.
Figure 1B:
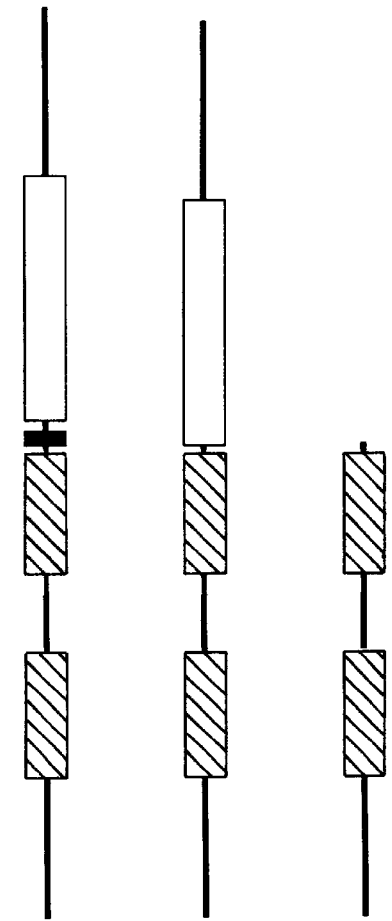

A first construct was accordingly prepared which deleted exactly in-frame the 22 amino acid transmembrane spanning sequence of HER2, and 3 amino acids on either side (FIG. 1). The construct was prepared as follows:

The central EcoRl fragment containing the transmembrane spanning segment was cloned into the EcoRl site of the bacteriophage vector M13 mpl8 (Yanisch-Perron et al., Gene, 33:103–119 (1985). The noncoding strand was used as template for oligonucleotide-directed mutagenesis. The construct deleted the transmembrane spanning sequence, and an additional 3 amino acids before and after.

Residues 651–678 were deleted by priming double stranded DNA synthesis with a 30 base pair oligonucleotide of sequence 5' CAG AGA GCC AGC CCT CAG CAG AAG ATC CGG 3'. The double stranded DNA was transformed into SR101 cells and mutants identified by hybridization to the same oligonucleotide 5' end labeled by polynucleotide kinase and [γ-$^{32}$P] ATP (Amersham, 5000 Ci/mmol). An EcoRl fragment containing the deletion was recombined into a plasmid expressing the HER2 cDNA, replacing the wild type sequence.

Figure 2:
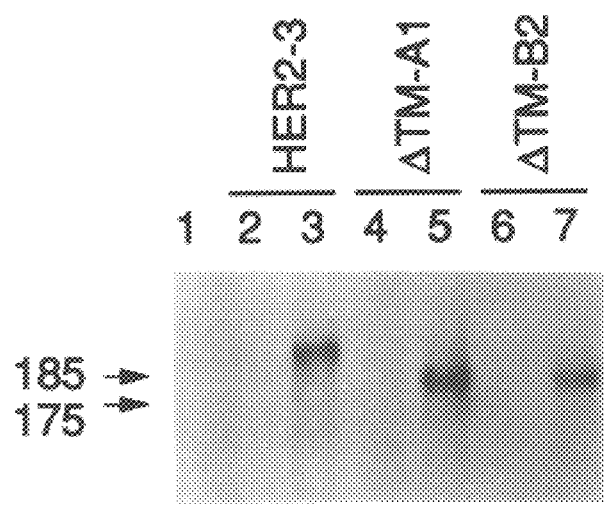
FIG. 2. Amplification of HER2 and HER2ΔTM genes. Cell lines transfected with plasmids expressing wild type or the ΔTM mutant HER2 cDNAs were amplified to resistance to 400 nM methotrexate. Cultures were metabolically labeled with [$^{35}$S]-methionine and proteins immunoprecipitated with the G-H2CT17 antibody. Lane 1: CVN-transfected NIH 3T3 vector control line. Lanes 2 and 3: Parental and amplified HER2-3 line. Lanes 4, 5, and 6, 7: Parent and amplified lines derived from two independent clones, A1 and B2, of the ΔTM mutant. The arrows indicate the positions expected for proteins of apparent molecular mass of 175 and 185 kDa.

When expressed in NIH 3T3 cells, this mutant, designated HER2$^{\Delta TM}$, produced a polypeptide, designated p185$^{HER2}$ ΔTM, of apparent molecular weight 175 kD (FIG. 2, lanes 5 and 7). Production took place at levels comparable to wild type p185$^{HER2}$ amplified to the same level of resistance to methotrexate (FIG. 2, lane 3). The mutant proteins also retained an active tyrosine kinase activity.

Figure 3:
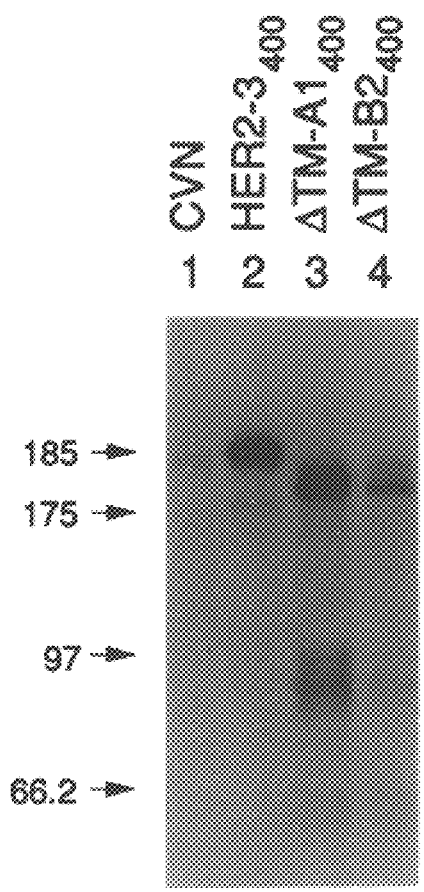
FIG. 3. Autophosphorylation of p185$^{HER2}$ and p185$^{HER2\Delta TM}$ proteins. Triton X-100 lysates of control, HER2-3$_{400}$, and ΔTM-expressing cell lines were prepared and immunoprecipitated with the G-H2CT17 antibody. The immune complexes were incubated in 50 ul of HNTG, 5 mM MnCl2 with 3 uCi [γ-$^{32}$P] for 20 min, electrophoresed on a 7.5% polyacrylamide gel, and labeled bands visualized by autoradiography. Lane 1: CVN vector control. Lane 2: HER2-3$_{400}$ cells expressing full-length HER2. Lanes 3 and 4: Two independent lines expressing p185$^{HER2\Delta TM}$. The arrows indicate the positions expected for proteins of apparent molecular mass of 66.2, 97, 175, and 185 KDa.

In the presence of [γ-$^{32}$P]-ATP, the mutant proteins (FIG. 3, lanes 3 and 4) were autophosphorylated to the same extent as unaltered p185$^{HER}$ (FIG. 3, lane 2). FIG. 3 also shows autophosphorylated p185$^{HER2\Delta TM}$-related proteins of lower molecular weight than the complete protein. These smaller proteins may represent degradation products and, since they are not observed with p185$^{HER2}$, could imply a difference in intracellular processing of the mutant form.

To determine whether the form lacking the transmembrane sequence was secreted, cells were metabolically labeled with $^{35}$S-methionine. The culture conditions used herein were as follows: cells were cultured in a 1:1 mixture of Dulbecco's modified Eagle's medium and Ham's nutrient mixture F-12 supplemented with glutamine (2 mM), penicillin (100 units/ml), streptomycin (100 ug/ml), and 10% serum. NIH 3T3-derived cell lines were cultured with calf serum (Hyclone). Chinese Hamster Ovary cells deficient in dihydrofolate reductase (CHO-DHFR) were cultured in fetal bovine serum (Gibco) supplemented with glycine (0.13 mM), hypoxanthine (0.11 mM), and thymidine (0.02 mM). (For selection of the transfected plasmid DHFR gene or to amplify introduced plasmids by methotrexate selection, the glycine, hypoxanthine, and thymidine were omitted and extensively dialyzed serum substituted for fetal bovine serum.)

Figure 4:
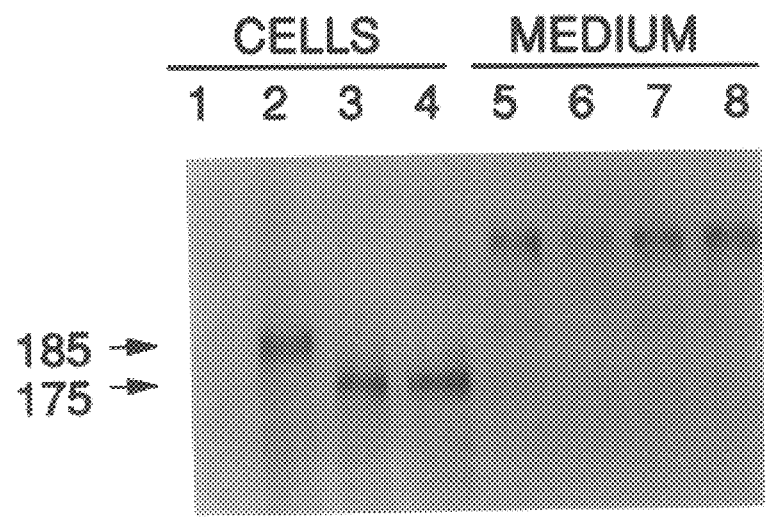
FIG. 4. Secretion assay of ΔTM mutants. Cell lines CVN, HER2-3$_{400}$, ΔTM-A1$_{400}$, and ΔTM-B2$_{400}$ were labeled with [$^{35}$S]-methionine overnight. Triton X-100 cell extracts were prepared and the labeling medium collected. Cells and cell-conditioned media were immunoprecipitated with G-H2CT17 antibody and analyzed on 7.5% SDS-PAGE gels. Lanes 1–4 are immunoprecipitations of cell extracts from the various lines, and lanes 5–8 are immunoprecipitations from the corresponding cell-conditioned media. Lanes 1 and 5: CVN vector control. Lanes 2 and 6: HER2-3$_{400}$ cell lines expressing full-length p185$^{HER2}$. Lanes 3, 4 and 7, 8:ΔTM-A1$_{400}$ and ΔTM-B2$_{400}$ cell lines expressing mutant p185$^{HER2\Delta TM}$. The arrows indicate the positions expected for proteins of apparent molecular mass of 175 and 185 KDa.

Both cells and cell-conditioned medium were assayed for p185$^{HER2}$. FIG. 4 demonstrates that all p185$^{HER2}$ remained cell associated (lanes 2, 3, 4), and neither the wild type protein nor the mutant form was secreted (lanes 6, 7, 8).

Thus, contrary to expectations, deletion of the transmembrane spanning sequence was not sufficient to yield a secreted form of p$_{185}$$^{HER2}$.

The discovery that p185HER$^{2\Delta TM}$ is not secreted suggested that perhaps there are sequences distal to the transmembrane spanning region that prevent passage of p185$^{HER2}$ through the plasma membrane. A second mutant was accordingly made that contained a UAA stop codon 8 amino acids before the beginning of the proposed transmembrane spanning sequence (FIG. 1).

The second construct truncated p185$^{HER2}$ 8 amino acids before the start of the transmembrane spanning region at residue 645 by addition of a polypeptide chain-terminating TAA codon. The oligonucleotide 5' AAG GGC TGC CCC GCC GAG TAA TGA TCA CAG AGA GCC AGC CCT 3' was used to prime synthesis of double-stranded DNA from the same template used to construct the ΔTM mutant. Mutant plaques were identified by hybridization to the 5' end-labeled oligonucleotide, and confirmed by checking for the presence of a Bcl 1 site also introduced directly after the ochre codon. The chain-terminated mutant, designated HER2$^{XCD}$, was then recombined into the HER2 cDNA expression plasmid. The structure of the plasmid and the 2 mutant HER2 derivatives is shown in FIG. 1.

Secretion of the resulting form of p185$^{HER2}$, designated p185$^{HER2XCD}$, was assayed by first metabolically labeling the cells with $^{35}$S-methionine, followed by immunoprecipitation of p185$^{HER2}$-related proteins from both the cells and cell-conditioned media. In the immunoprecipitation procedure (Hudziak et al., Proc. Natl. Acad. Sci. USA, 84:7159–7163 (1987)), cells were harvested by trypsinization, counted electronically with a Coulter counter, and plated at least 6 hrs. before labeling. The plating medium was removed, cells washed with PBS, and the cells re-fed with methionine-free Dulbecco's modified minimal medium. [$^{35}$S]-methionine (Amersham, 800 Ci/mmol, 29.6 TBg/mmol) was added at 100 uCi/6 cm plate in a volume of 3 ml. Cells were lysed at 4° C. with 0.4 ml of HNEG lysis buffer per 6 cm plate. After 10 min, 0.8 ml of lysis dilution buffer (HNEG buffer with 1% bovine serum albumin, 0.1% Triton X-100 detergent) was added to each plate and the extracts were clarified by microcentrifugation for 5 min. Medium to be assayed for secretion of p185$^{HER2}$ related proteins was collected and clarified by microcentrifugation.

Antibodies were added to cell extracts or conditioned medium and allowed to bind at 4° C. for 2–4 h. The polyclonal antibody, G-H2CT17(0), recognizing the carboxy-terminal 17 amino acids of p185$^{HER2}$, was used for characterization of cell lines expressing the transmembrane-deleted form of p185$^{HER2}$. The monoclonal antibody 3E8, recognizing an epitope on the extracellular domain (Hudziak et al., *Mol. Cell. Bio.*, 9:1165–1172 (1989)), was used at 8 ug/reaction to immunoprecipitate the truncated form. Seven ug of rabbit anti-mouse IgG was added to immunoprecipitations using this monoclonal to improve its binding to protein A-sepharose. Immune complexes were collected by absorption to protein A-sepharose beads and washed (Hudziak et al., *Proc. Natl. Acad. Sci. USA*, 85:5102–5106 (1988); Hudziak et al., *Proc. Natl. Acad. Sci. USA*, 84:7159–7163 (1987)). Proteins were separated on 7.5% sodium dodecyl sulphate-polyacrylamide gels (SDS-PAGE) and analyzed by autoradiography.

Figure 5:
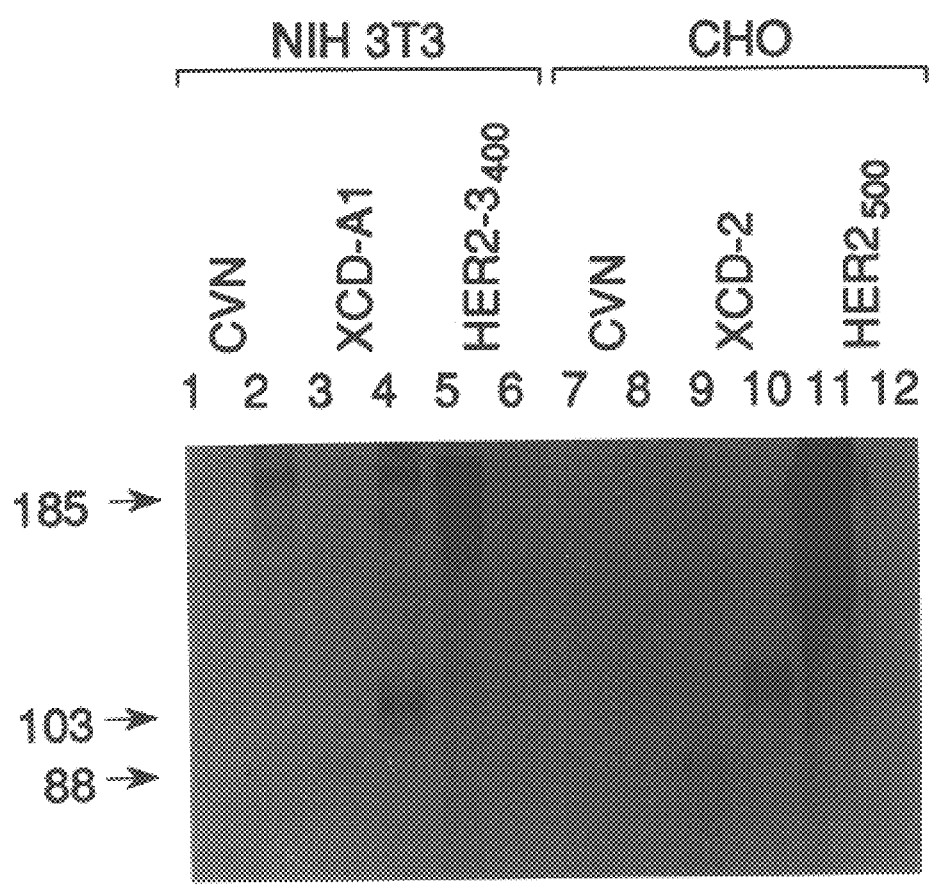
FIG. 5. Secretion of p185$^{HER2XCD}$ from 3T3 and CHO cells. NIH 3T3 and CHO cell lines expressing full-length and truncated p185$^{HER2}$ and vector controls were labeled with [$^{35}$S]-methionine overnight. Cell extracts and cell-conditioned media were immunoprecipitated with anti-HER2 monoclonal antibody 3E8 and analyzed on 7.5% SDS-PAGE gels. Lanes 1 and 2: NIH 3T3 control cell line, extract and conditioned medium. Lanes 3 and 4: NIH 3T3 line A1 expressing p185$^{HER2XCD}$, cells and medium. Lanes 5 and 6: NIH 3T3 line 3$_{400}$ expressing full-length p185$^{HER2}$, cells and conditioned medium. Lanes 7 and 8: CHO control line, cell extract and conditioned medium. Lanes 9 and 10: CHO line 2, expressing p185$^{HER2XCD}$, cells and conditioned medium. Lanes 11 and 12: CHO line HER2$_{500}$, expressing full-length p185$^{HER2}$, cells and conditioned medium. The arrows indicate the molecular mass of the indicated protein bands.

This revealed a form of p185$^{HER2XCD}$ of $M_r$ 88,000 kD that is associated with the cells (FIG. 5, lanes 3 and 9); however, the cell-conditioned media from both the NIH 3T3 cells and Chinese hamster ovary-derived lines also contains larger amounts of a protein of $M_r$ 103,000, which is immunoprecipitated by anti-HER2 monoclonal antibody (FIG. 5, lanes 4 and 10). Full length p185$^{HER2}$ was also expressed in both NIH 3T3 and CHO cells (FIG. 5), lanes 5 and 11. There is no secretion of native p185$^{HER2}$ from either of these cell types (FIG. 5, lanes 6 and 12).

The larger size of the observed proteins in the cells and cell-conditioned medium (88,000 and 103,000, respectively) compared to the size predicted by the amino acid sequence (71,644) suggested that the truncated form was being glycosylated.

Figure 7:
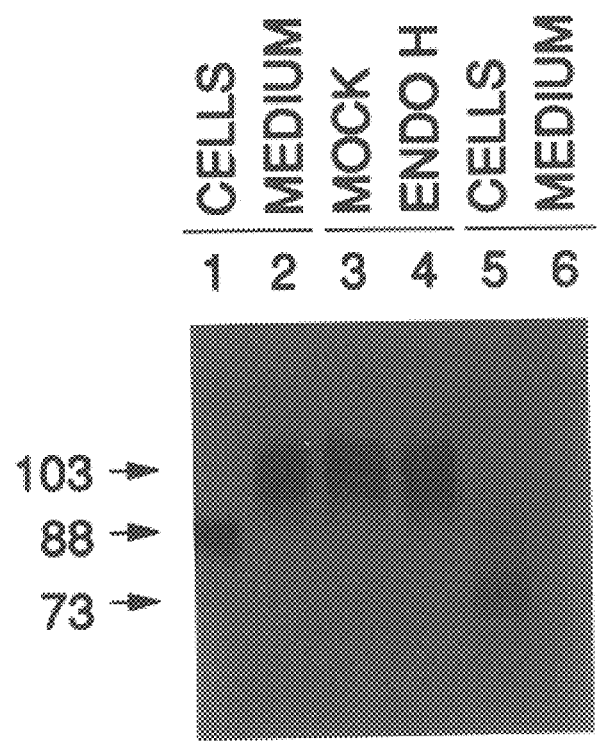
FIG. 7. Biosynthesis of p185$^{HER2XCD}$. The CHO line HER2XCD2$_{3000}$ was labeled with [$^{35}$S]-methionine and cell extracts, and cell-conditioned media prepared. Lanes 1 and 2: Cell extract and cell-conditioned medium. Lanes 3 and 4: The same conditioned medium incubated or mock-incubated with endo H. Lanes 5 and 6: Cell extract and conditioned medium from cells treated with tunicamycin. The arrows show the positions expected for proteins of apparent molecular mass of 73, 88, and 103 KDa.
Figure 8A:
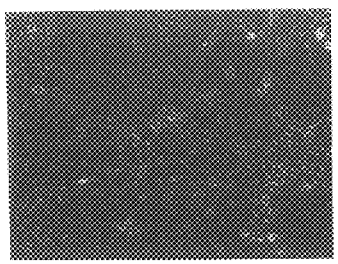
FIGS. 8A–8F. Morphology of NIH 3T3 cells transfected with HER2 and HER2ΔTM expression constructs. A and D: Parental and amplified cells from NIH 3T3 cells transfected with vector alone. B and E: NIH 3T3 cells expressing p185$_{HER2\ \Delta TM}$ (line A1), parent and amplified derivative selected for resistance to 400 nM methotrexate. C and F: NIH 3T3 cells expressing wild type p185$^{HER2}$ (line 3), parent and amplified derivative selected for resistance to 400 nM methotrexate.
Figure 8B:
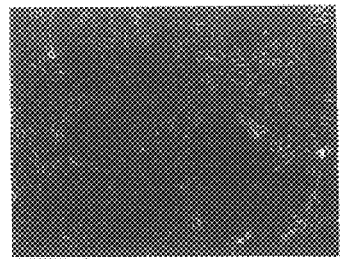
Figure 8C:
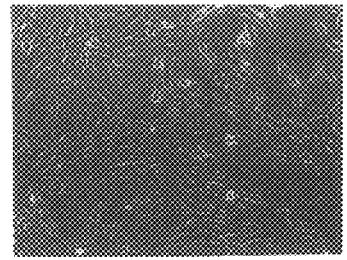
Figure 8D:
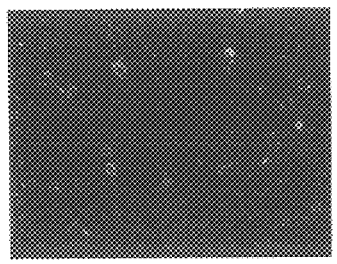
Figure 8E:
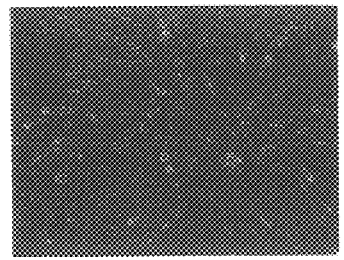
Figure 8F:
Figure 9A:
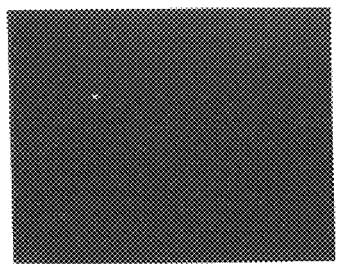
FIGS. 9A–9F. Cell surface and cytoplasmic immunofluorescence staining of control, HER2, and HER2ΔTM lines. The top photos are intact cells labeled with anti-HER2 monoclonal antibody. The bottom photos are the same cell lines treated with 0.15% Triton X-100 detergent before addition of antibody. A and D: Control NIH 3T3 cells transfected with vector only. B and E: Cell line HER2 ΔTM-A1$_{400}$, expressing p185HER2ΔTM. C and F: Cell line HER2-3$_{400}$ expressing p185$^{HER2}$.
Figure 9B:
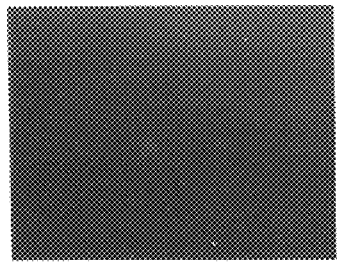
Figure 9C:
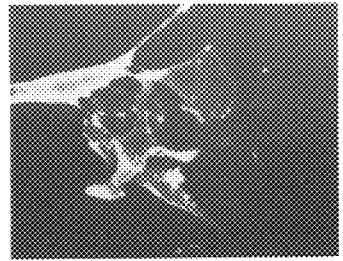
Figure 9D:
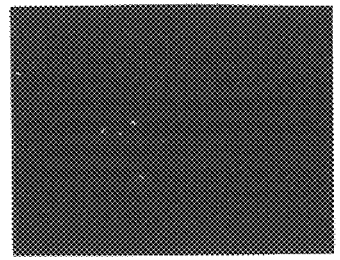
Figure 9E:
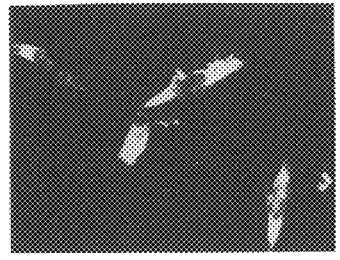
Figure 9F:
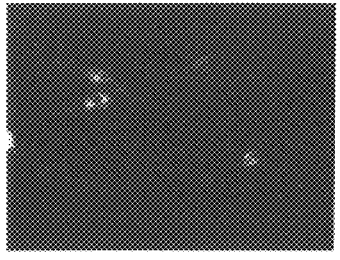
Figure 10A:
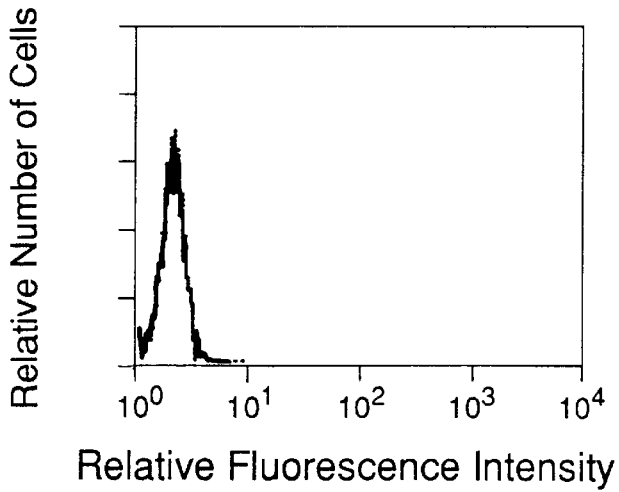
FIGS. 10A–10C. Fluorescence-activated cell sorter histograms of control, HER2 and HER2ΔTM cells binding anti-p185$^{HER2}$ monoclonal antibody 4D5. Binding by the control antibody, 368, directed against human tissue plasminogen activator, light, broken line. Binding by the anti-HER2 antibody 4D5, dark unbroken line. Panel A: Control NIH 3T3 cells transfected with vector only. Panel B: Cell line HER2-3$_{400}$, expressing p185$^{HER2}$. Panel C: Cell line HER2 ΔTM A1$_{400}$ expressing p185$^{\Delta TM}$.
Figure 10B:
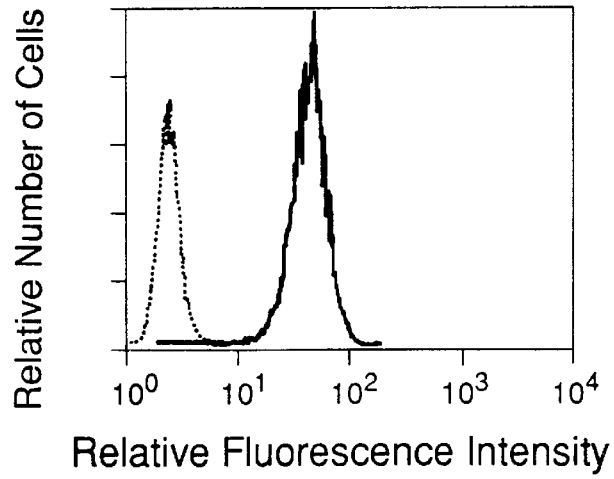
Figure 10C:
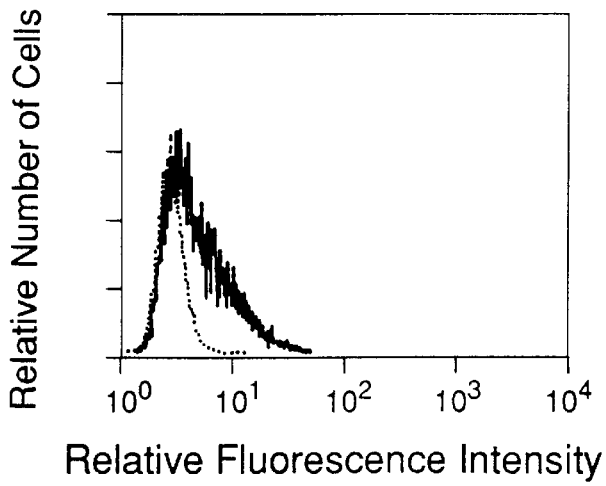
Figure 11:
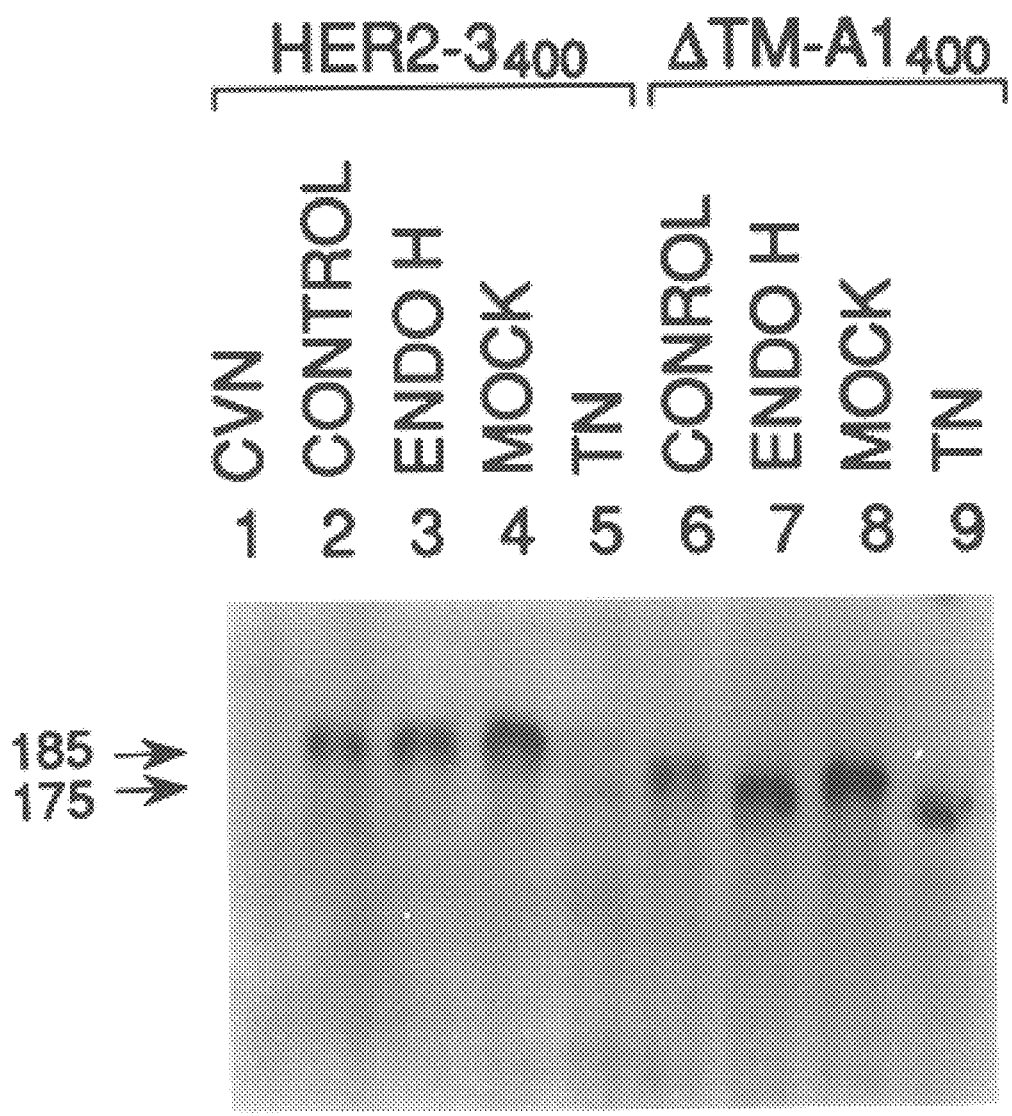
FIG. 11. Biosynthesis of p185$^{HER2}$ and p185$^{HER2\Delta TM}$ proteins. Cell lines HER2-3$_{400}$ and HER2 ΔTM-A1$_{400}$ were labeled with [$^{35}$S]-methionine and p185$^{HER2}$ and p185$^{HER2\Delta TM}$ proteins collected by immunoprecipitation and analyzed on a 7.5% SDS- PAGE gel. Lane 1: Vector control. Lane 2: Untreated p185$^{HER2\Delta TM}$. Lanes 3 and 4: Aliquots of the same cell extract treated or mock-treated with endo H. Lane 5: Nonglycosylated p185$^{HER2}$ from cells treated with tunicamycin. Lane 6: Untreated p$_{185}$$^{HER2}$. Lanes 7 and 8: Aliquots of the same cell extract treated or mock-treated with endo H. Lane 9: Nonglycosylated p185$^{HER2\Delta TM}$ from cells treated with tunicamycin. The arrows show the positions of proteins of apparent molecular weight of 175 and 185 kDa.

This was confirmed by treating the cells with the antibiotic tunicamycin, which prevents N-linked glycosylation. Treatment with tunicamycin resulted in the appearance of a cell-associated protein of $M_r$ 73,000, which is close to that predicted by the amino acid sequence (FIG. 7, lane 5). It also almost completely inhibited secretion of p185$^{HER2XCD}$ into the medium (FIG. 7, lane 6). Cell-conditioned medium from tunicamycin treated cells contains only small amounts of the mature 103,000 form, and none of the smaller forms (lane 6). This further suggests that secretion of p185$^{HER2XCD}$ is coupled to glycosylation.

The extent of glycosylation of the secreted form was investigated with the enzyme endoglycanase H (endo H, Boehringer Manheim). This enzyme will hydrolyze asparagine-linked oligosaccharides of the high mannose type. High mannose oligosaccharides are biosynthetic intermediates in the glycosylation process. Final maturation of the carbohydrate side chains involves trimming off some mannose and addition of other sugars such as fucose. Such mature oligosaccharide side chains are resistant to endo H.

To determine if secreted p185$^{HER2XCD}$ is resistant to this enzyme, cell conditioned medium labeled with $^{35}$S-methionine was immunoprecipitated. The immunoprecipitates were collected onto protein A sepharose beads and incubated with endo H. Neither mock incubated (lane 3) nor endo H-treated p185$^{HER2XCD}$ (lane 4) showed any decrease in mobility associated with hydrolysis of the glycosyl side chains, demonstrating that the glycosylation is complete.

Without being bound by any particular theory, these results taken together suggest that the cell-associated form of p185$^{HER2XCD}$ is an intermediate, and that fully mature glycosylated p185$^{HER2}$ extracellular domain is being synthesized and secreted. The lack of secretion of the p185$^{HER2\Delta TM}$ protein could be hypothesized to result from the presence of processing information in the transmembrane spanning sequence which is necessary for Golgi transport and targeting of the plasma membrane; however, from these studies it appears instead that transport of tyrosine kinase receptor (or receptor-like) extracellular domain to the cell surface is coupled to proper glycosylation.

Therefore, insertion of the UAA stop codon 8 amino acids before the beginning of the proposed transmembrane spanning sequence yields a fully mature glycosylated p185$^{HER2}$ extracellular domain which is freely secreted by the cell.

Figure 6:
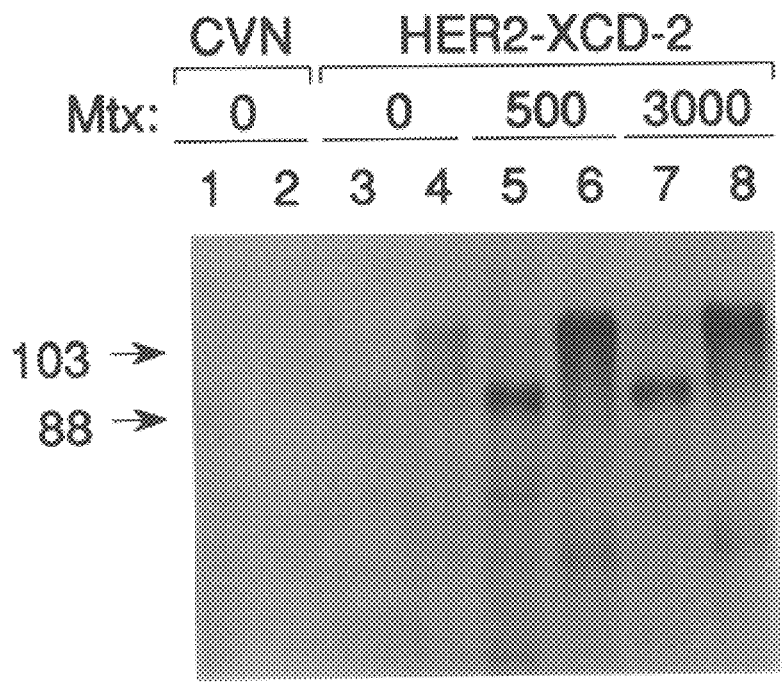
FIG. 6. Increase in expression of p185$^{HER2XCD}$ with amplification. The CHO-derived cell line HER2XCD-2 was selected for growth in 500 nM and then 3000 nM methotrexate. The parent line, the two amplified derivatives, and control vector-transfected cells were labeled with [$^{35}$S]-methionine. Cell extracts and cell-conditioned media were immunoprecipitated with the anti-HER2 monoclonal antibody 3E8 and analyzed on a 7.5% SDS-PAGE gel. Lanes 1 and 2: CVN cell extract and conditioned medium. Lanes 3 and 4: HER2XCD-2, unamplified cells and conditioned medium. Lanes 5 and 6: HER2XCD-2 amplified to resistance to 500 nM methotrexate, cells and conditioned medium. Lanes 7 and 8: HER2XCD-2 amplified to resistance to 3000 nM methotrexate, cells and conditioned medium. For comparative purposes, one-fifth as much sample of the 3000 nm line was loaded compared to the control, 0 nM, and 500 nM lines. The band intensities were quantitated with an LKB2202 laser densitometer. The arrows show the positions of proteins of apparent molecular mass of 88 and 103 KDa.

Having succeeded in producing a secreted form of p185$^{HER2}$, the next stage involved investigating whether the amount of secreted protein could be increased by gene amplification. Using the CHO-derived cell line, it was found that the amount of extracellular domain could be increased by methotrexate selection. The amount of secreted product increased 29-fold in cells selected for resistance to 500 nm methotrexate, and a further 4.4-fold by selection for resistance to 3000 nm methotrexate (FIG. 6).

Thus, a total increase of 128-fold in secreted p185$^{HER2XCD}$ was obtained when this cell line was amplified to resistance to 3000 nm methotrexate, making the production of relatively large quantities of p185$^{HER2XCD}$ possible.

To determine whether overexpression of p185$^{HER2\Delta TM}$ results in cell transformation, DNA was introduced in mammalian cells by the CaHPO$_4$ coprecipitation method (Graham et al., *Virology*, 52:456–467 (1973)). Five ug of plasmid DNA was added to half-confluent plates of cells (6.0 cm) in 1 ml for 4–6 h. The DNA was removed and the cells shocked with 20% (vol/vol) glycerol. After 2 days for phenotypic expression the selective agent geneticin was added at 400 ug/ml. Clones were picked using glass cloning cylinders with petroleum jelly for the bottom seal. The introduced plasmids were amplified by the methotrexate selection procedure (Kaufman et al., *J. Mol. Biol.*, 159:601–621 (1982)).

When the ΔTM mutant was expressed in NIH 3T3 cells, primary unamplified colonies after selection had the normal flat nontransformed phenotype (FIG. 8, compare photo B with vector control alone, photo A). After the expression level was increased by methotrexate selection, the cells took on the refractile, spindle-shaped appearance of transformed cells and also grew piled up in irregular clumps (photo E). This observation is similar to our earlier findings with the unaltered HER2 cDNA (photos C and F, parent and amplified derivatives respectively), and suggests that high levels of expression of the mutant ΔTM protein were also transforming.

The morphological changes seen at equivalent levels of amplification (400 nm methotrexate) are not as marked for the mutant, implying that the transforming potential of this form of p185$^{HER2}$ may be less. At higher levels of resistance to methotrexate, the ΔTM cells become even more transformed in appearance.

The plasmid was also negative in a focus-forming assay whereas the wild type HER2 plasmid was positive, further indicating that the transforming potential of $p185^{HER2\Delta TM}$ protein is lower. Cells expressing high levels also displayed another property of the transformed phenotype, growth in soft agar. Colony formation in soft agar was determined by harvesting each line to be assayed with trypsin, counting the cells (Coulter counter), and plating 80,000 cells per 6-cm dish. The top layer consisted of 4 ml of 0.25% agar (Difco, "purified") over a bottom layer of 5 ml of 0.5% agar. Colonies were counted after 3–4 weeks. Cells from 2 independent clones plated in soft agar gave rise to soft agar colonies with an efficiency comparable to cells expressing the wild type HER2 gene:

TABLE I

Soft Agar Colony Formation

| Cell Line | # of Soft Agar Colonies |
| --- | --- |
| CVN | 0 |
| $CVN_{400}$ | 0 |
| $HER2-3_0$ | 5 +/− 1 |
| $HER2-3_{400}$ | 208 +/− 27 |
| $\Delta TM-A1_0$ | 0 |
| $\Delta TM-A1_{400}$ | 205 +/− 62 |
| $\Delta TM-B2_0$ | 0 |
| $\Delta TM-B2_{400}$ | 205 +/− 13 |

Two control lines were used; NIH 3T3 cells transfected with a plasmid expressing only the neo and DHFR genes, and the same line amplified to resistance to 400 nM methotrexate. The number of soft agar colonies arising was determined for both parental and amplified lines of clones expressing either $p185^{HER2}$ or $p185^{HER2\Delta TM}$ proteins. Each cell line was plated in triplicate and the value averaged.

Therefore, according to the present invention it has been determined that removal of only the transmembrane spanning sequence does not lead to secretion of $p185^{HER2}$, unless the entire tyrosine kinase domain is also deleted. Removal of this domain results in proper glycosylation and secretion of the extracellular domain.

In order to obtain purified HER2 extracellular domain working material, Chinese Hamster Ovary Cell Harvest Fluid (CFF) containing recombinant HER2 ECD may be first concentrated by ultrafiltration, and then purified by immunoaffinity chromatography using a HER2 specific MAb coupled to CNBr activated Sepharose; other suitable immobilization supports may be used. Concentrated CCF is applied to the affinity column after filtration through a 0.2 micron Millipor filter. Purification cycles are performed as necessary until the desired amount of CCF is processed.

During each cycle of purification, the concentrated CCF is applied and the affinity column is washed to baseline with 0.5 M Tris buffer containing 0.15 M NaCl at a pH of approximately 7.5 (TB). HER2 extracellular domain is then eluted from the column with 0.1 M sodium citrate buffer containing 0.5 M NaCl at a pH of approximately 3.5. The affinity column eluant fractions containing HER2 ECD are pooled and neutralized. The immunoaffinity column is reequilibrated between each purification cycle with TB.

In a second step, the affinity column eluant is buffer exchanged into 25 ml of Tris buffer, at a pH of approximately 7.0 (TB2). The HER2 extracellular domain is then applied to a DEAE Sepharose Fast Flow column, and washed with TB2. The HER2 ECD is removed from the column by step or gradient salt elution in TB2 (containing up to 200 mM NaCl).

Figure 12:
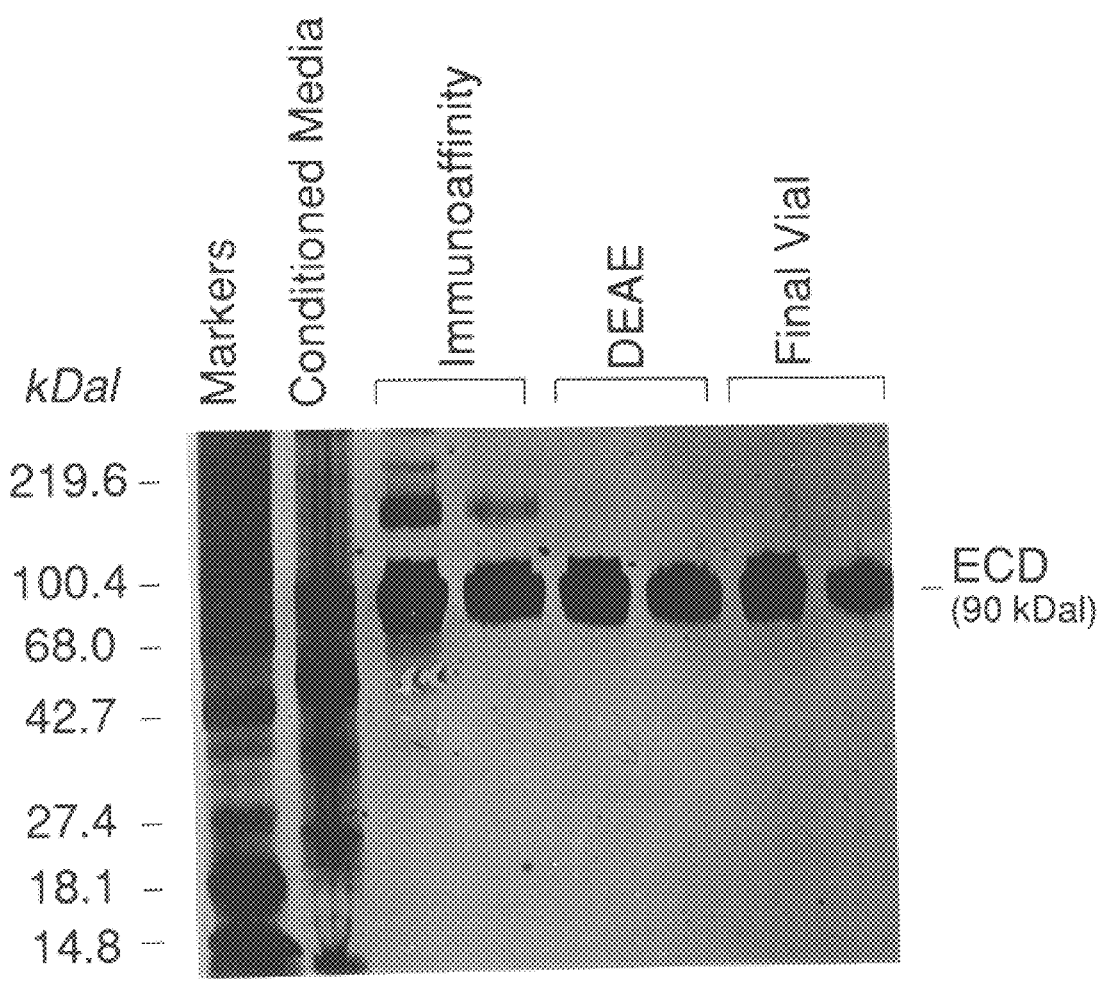
FIG. 12. Purification of the HER2 extracellular domain. Purified HER2 extracellular domain samples were analyzed using PhastSystem SDS-Gel electrophoresis and silver stained protocols as recommended by Pharmacia. SDS polyacrylamide gel (10–15% gradient) electrophoretic analysis was performed according to Pharmacia protocol File No. 110. Silver staining was performed according to Pharmacia protocol File No. 210. Lane 1 contains molecular weight markers (BRL). Lane 2: Chinese Hamster Ovary Cell 15 X concentrate (1 microliter). Lanes 3 and 4: immunoaffinity purified HER2 extracellular domain (1.6 micrograms and 0.16 microgram, respectively). Lanes 5 and 6: immunoaffinity purified HER2 extracellular domain after DEAE chromatography (0.25 micrograms and 0.083 micrograms, respectively). Lanes 7 and 8: HER2 extracellular domain after formulation in PBS (0.32 micrograms and 0.082 micrograms, respectively).

After DEAE chromatography, purified HER2 ECD fractions are pooled, exchanged into phosphate-buffered saline, and stored at 2–8° C. The resulting material is substantially pure, i.e., about 99% pure (see FIG. 12).

By means of the present invention it is accordingly possible to produce a secreted, glycosylated $p185^{HER2}$ extracellular domain. This opens several possibilities for further research, as well as a broad range of potential therapeutic applications.

As previously stated, the HER2 gene is of particular interest because its amplification has been correlated with certain types of cancer. In a survey of 189 primary mammary gland adenocarcinomas, it was found that 30% contained amplifications of the HER2 gene. Slamon et al., "Human Breast Cancer: Correlation of Relapse and Survival with Amplification of the HER-2/neu Oncogene," Science 235, 177–182 (1987). Amplification was correlated with a negative prognosis and high probability of relapse.

This suggests that of the 120,000 women diagnosed with breast cancer each year, 36,000 will have HER2 amplification. Approximately half of these women, or about 15,000, may be expected to exhibit greater than 5-fold amplification, corresponding to nearly half of the 40,000 breast cancer-related deaths each year.

It has been demonstrated that a monoclonal antibody directed against the $p185^{HER2}$ extracellular domain specifically inhibits growth of breast tumor-derived cell lines overexpressing the HER2 gene product; prevents HER2-transformed NIH 3T3 cells from forming colonies in soft agar; and reduces the resistance to the cytotoxic effect of tumor necrosis factor alpha which accompanies HER2 overexpression. Hudziak et al., "$p185^{HER2}$ Monoclonal Antibody has Antiproliferative Effects In Vitro and Sensitizes Human Breast Tumor Cells to Tumor Necrosis Factor", Mol. Cell. Biol. 9:1165–1172 (1989). See also, Drebin et al., "Inhibition of Tumor Growth by a Monoclonal Antibody Reactive with an Oncogene-Encoded Tumor Antigen", Proc. Natl. Acad. Sci. USA 83, 9129–9133 (1986) (in vivo treatment with anti-p185 monoclonal antibody asserted to inhibit tumorigenic growth of neu-transformed NIH 3T3 cells implanted in mice).

This effect presents the possibility that conditions characterized by amplification of the HER2 gene may be subject to treatment via Active Specific Immunotherapy. This therapeutic modality contemplates provoking an immune response in a patient by vaccination with an immunogenic form of the extracellular domain. The extracellular domain (or a derivative thereof, as discussed below) may be combined with a local adjuvant which is safe and effective in humans, such as alum, Bacillus calmette-Guerin (BCG), adjuvants derived from BCG cell walls, Detox (Ribi-immunochem), Syntex-1, or Corynebacterium parvum. Alternatively, systemic adjuvants, such as Interferon gamma, Interleukin 1, Interleukin 2, or Interleukin 6 may be suitable. An appropriate dose and schedule would be selected to maximize humoral and cell-mediated response.

It may also be possible to enhance an immune response by targeting the immunogen to the immune system, which could lead to more efficient capture of the antigen by antigen presenting cells, or by directing the immunogen so that it is presented by MHC Class 1 molecules, since these usually induce a T-cell response.

In addition to Active Specific Immunotherapy, it should be possible to use the purified extracellular domain to isolate and characterize the putative ligand. The HER2 ligand may be used in turn to deliver toxin to tumor cells which are overexpressing HER2, such as by molecular fusion of the ligand with toxin, or by chemical cross-linking.

Alternatively, patients overexpressing HER2 may be vaccinated with HER2 ligand conjugated to, or in combination with, a suitable adjuvant.

A patient overexpressing HER2 will also presumably be overexpressing the HER2 ligand. The ligand-HER2 binding interaction, which is likely to contribute to tumor growth, may be inhibited by blocking free ligand in the patient's serum. This blocking can be accomplished by treating the patient with the HER2 extracellular domain, which will proceed to bind free HER2 ligand, thereby preventing the ligand from binding to the HER2 receptor site.

Rather than using the HER2 extracellular domain per se, it may be more desirable to use a derivative which has an increased affinity for the ligand, and/or which has an increased half-life in vivo. Cross-linking on cells is known to improve binding affinity, suggesting that artificial cross-linking can be used to improve the binding ability of the HER2 extracellular domain. The half-life of the extracellular domain in serum can be improved by, for example, fusing the extracellular domain with other molecules present in the serum which are known to have a long half-life, such as the Fc-portion of an immunoglobin molecule.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

What we claim is:

1. A process for producing a secreted, glycosylated extracellular domain of the HER2 receptor, comprising the steps of:
   (a) culturing an eukaryotic host comprising DNA encoding the extracellular domain, wherein said DNA terminates 1 base pair to about 24 base pairs upstream of DNA encoding the transmembrane domain of said HER2 receptor, under conditions suitable for expression of said DNA and secretion of said extracellular domain; and
   (b) isolating said extracellular domain from said host, wherein said isolated exracellular domain is immunogenic in a human and provokes a humoral and cell-mediated response against HER2 receptor upon administration to a patient.

2. The process of claim 1 wherein the DNA in step (a) terminates about 24 base pairs upstream of the DNA encoding the transmembrane domain of said HER2 receptor.

3. The process of claim 1 wherein said isolated extracellular domain at step (b) has a molecular weight of about 103 kD.

4. A method for making a polypeptide fusion comprising an extracellular domain of the HER2 receptor conjugated to a Fc portion of an immunoglobulin molecule, comprising:
   (a) culturing a host cell comprising DNA encoding said polypeptide fusion under conditions suitable for expression of said DNA; and
   (b) recovering said polypeptide fusion from said host cell.

5. The method of claim 4 wherein said host cell in step (a) is a prokaryote.

6. The method of claim 5 wherein said prokaryote is a bacterium.

7. The method of claim 4 wherein said host cell in step (a) is a eukaryote.

8. A method for making a vaccine useful for Active Specific Immunotherapy, comprising:
   (a) culturing a host cell comprising DNA encoding the extracellular domain of the HER2 receptor or a portion thereof which provokes a humoral and cell-mediated response against HER2 receptor in a patient vaccinated therewith under conditions suitable for expression of said DNA;
   (b) recovering said extracellular domain or portion thereof from said host cell; and
   (c) combining said recovered extracellular domain or portion thereof with an adjuvant which is safe and effective in humans so as to generate a vaccine which provokes a humoral and cell-mediated response against HER2 receptor in a patient vaccinated therewith.

9. The method of claim 8 wherein the adjuvant at step (c) is selected from the group consisting of alum, *Bacillus calmette*-Guerin (BCG), an adjuvant derived from BCG cell walls, Detox, Syntex-1, *Corynebacterium parvum*, interferon gamma, interleukin 1, interleukin 2 and interleukin 6.

10. The method of claim 8 wherein the DNA in step (a) encodes the extracellular domain portion thereof conjugated to a peptide having immunogenic properties in a human.

11. The method of claim 8 wherein said host cell in step (a) is a prokaryote.

12. The method of claim 11 wherein said prokaryote is a bacterium.

13. The method of claim 8 wherein said host cell in step (a) is a eukaryote.

14. The method of claim 13 wherein said extracellular domain or portion thereof covered at step (b) is glycosylated.

15. The method of claim 8 wherein said DNA in step (a) encodes said extracellular domain of the HER2 receptor.

16. The method of claim 8 wherein said DNA in step (a) encodes said portion of the extracellular domain of the HER2.

* * * * *

UNITED STATES PATENT AND TRADEMARK OFFICE
CERTIFICATE OF CORRECTION

PATENT NO. : 6,333,169 B1
DATED : December 25, 2001
INVENTOR(S) : Robert Michael Hudziak et al.

It is certified that error appears in the above-identified patent and that said Letters Patent is hereby corrected as shown below:

Title page,
Item [75], Inventors "Robert Michael Hudziak; H. Michael Shepard; Axel Ullrich, all of 460 Point San Bruno, San Francisco, CA (US) 94080" should read
-- Robert Michael Hudziak, San Bruno; H. Michael Shepard, San Francisco, both of Calif. (US); Axel Ullrich, Martinsried, Germany (DE) --.

Column 17,
Line 28, "exracellular" should read -- extracellular --.

Column 18,
Line 36, "domain portion thereof" should read -- domain or portion thereof --.

Signed and Sealed this

Twenty-second Day of October, 2002

Attest:

JAMES E. ROGAN
Attesting Officer  Director of the United States Patent and Trademark Office

UNITED STATES PATENT AND TRADEMARK OFFICE
CERTIFICATE OF CORRECTION

PATENT NO. : 6,333,169 B1
DATED : December 25, 2001
INVENTOR(S) : Robert Michael Hudziak et al.

It is certified that error appears in the above-identified patent and that said Letters Patent is hereby corrected as shown below:

<u>Title page,</u>
Item [75], Inventors, "Robert Michael Hudziak; H. Michael Shepard; Axel Ullrich, all of 460 Point San Bruno, San Francisco, CA (US) 94080" should read -- Robert Michael Hudziak, San Bruno; H. Michael Shepard, San Francisco, both of Calif. (US); Axel Ullrich, Martinsried, Germany (DE) --.

<u>Column 17,</u>
Line 28, "exracellular" should read -- extracellular --.

<u>Column 18,</u>
Line 36, "domain portion thereof" should read -- domain or portion thereof --.

Signed and Sealed this

Twenty-ninth Day of October, 2002

Attest:

JAMES E. ROGAN
Attesting Officer  *Director of the United States Patent and Trademark Office*

UNITED STATES PATENT AND TRADEMARK OFFICE
CERTIFICATE OF CORRECTION

PATENT NO.     : 6,333,169 B1
DATED          : December 25, 2001
INVENTOR(S)    : Robert Michael Hudziak et al.

It is certified that error appears in the above-identified patent and that said Letters Patent is hereby corrected as shown below:

<u>Title page,</u>
After the Inventors section, insert Item:

-- [73]  Assignee:  Genentech, Inc., South San Francisco, CA (US) --.

<u>Column 18,</u>
Line 45, "covered" should read -- recovered --.

Signed and Sealed this

Tenth Day of June, 2003

JAMES E. ROGAN
*Director of the United States Patent and Trademark Office*